(12) United States Patent
Choate

(10) Patent No.: US 7,547,286 B2
(45) Date of Patent: Jun. 16, 2009

(54) METHOD TO REDUCE INFLAMMATION AND TACTILE FINGER SENSATION DEFICIT DUE TO CARPAL TUNNEL SYNDROME OR ARTHRITIS

(76) Inventor: John I. M. Choate, c/o Rt 1, Box 260H, Seminole, OK (US) 74818

( * ) Notice: Subject to any disclaimer, the term of this patent is extended or adjusted under 35 U.S.C. 154(b) by 927 days.

(21) Appl. No.: 10/780,476

(22) Filed: Feb. 16, 2004

(65) Prior Publication Data

US 2005/0197539 A1 Sep. 8, 2005

(51) Int. Cl.
*A61B 19/00* (2006.01)
*A61B 5/00* (2006.01)
*A61B 5/103* (2006.01)
*A61B 5/117* (2006.01)
*B41J 29/00* (2006.01)
*G06Q 90/00* (2006.01)

(52) U.S. Cl. .................. 600/557; 600/300; 600/301; 600/595; 128/898; 128/897; 400/719; 705/500

(58) Field of Classification Search .............. 600/301, 600/557, 300, 595; 128/898, 897; 400/719; 705/500
See application file for complete search history.

(56) References Cited

U.S. PATENT DOCUMENTS

| | | | |
|---|---|---|---|
| 5,352,050 A | * | 10/1994 | Choate ............ 400/486 |
| 5,498,088 A | * | 3/1996 | Choate ............ 400/486 |
| 5,579,238 A | * | 11/1996 | Krugman ........... 702/41 |
| 5,626,429 A | * | 5/1997 | Choate ............ 400/487 |
| 5,718,590 A | * | 2/1998 | Choate ............ 434/227 |
| 5,745,376 A | * | 4/1998 | Barker et al. ......... 702/41 |
| 5,836,705 A | * | 11/1998 | Choate ............ 400/486 |
| 6,090,045 A | * | 7/2000 | Leahy et al. ......... 600/301 |
| 6,692,435 B1 | * | 2/2004 | Choate ............ 600/300 |
| 7,074,198 B2 | * | 7/2006 | Krullaards .......... 600/587 |
| 2001/0049482 A1 | * | 12/2001 | Pozos et al. ......... 600/587 |

\* cited by examiner

*Primary Examiner*—Max Hindenburg
*Assistant Examiner*—Jeffrey G Hoekstra

(57) ABSTRACT

An apparatus or method to accommodate disability and to improve the efficiency of the movement of the fingers, in order; A) to reduce 1) onset of symptoms of median nerve entrapment or carpal tunnel or repetitive stress syndromes, 2) tactile deficit in fingers, 3) inflammation in the carpal canal, 4) tendon excursion in the carpal canal, 5) finger flexion, 6) loss of nerve sensation, and 7) loss of tactile sensation; and B) to increase 1) therapy of medical and physical recovery and treatment, 2) tactile sensitivity of the fingers, 3) movement of the doral interossei muscles of the hand, 4) movement of the volar interossei palmar muscles of the hand, 5) movement of the lumbrical muscles of fingers, and 6) identification of cancer mass in subcutaneous tissue by palpation by self examination.

9 Claims, No Drawings ated disorders with hand and finger use. The report did not consider the beneficial effects of reduction in finger flexion by use of the Dvorak keyboard. The report did not differentiate employees who used Dvorak exclusively or who alternated keyboard style. The report did not consider the beneficial effects of placing "e" and "t" on the home row.

METHOD TO REDUCE INFLAMMATION AND TACTILE FINGER SENSATION DEFICIT DUE TO CARPAL TUNNEL SYNDROME OR ARTHRITIS

Pursuant to 37 CFR 1.71(e): A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCES TO RELATED APPLICATIONS (IF ANY.)

None.

STATEMENT AS TO RIGHTS TO INVENTIONS MADE UNDER FEDERALLY—SPONSORED RESEARCH AND DEVELOPMENT

None

References in parenthesis in the specification are to sources appended at the end.

BACKGROUND OF THE INVENTION

1. Field of the Invention

The present invention is directed to using and testing devices or compounds which reduce onset of symptoms of median nerve entrapment or carpal tunnel syndrome or repetitive stress syndrome, reduce tactile deficit of fingers, and increase identification of foreign mass in breast and other self examinations, disability accommodation, medical and physical therapy, cancer discovery and prevention. Devices will improve the movement of the fingers, reduce the inflammation in the carpal canal, reduce the tendon excursion in the carpal canal, reduce finger flexion, reduce loss of nerve sensation, reduce loss of tactile sensation, increase tactile sensitivity of the fingers, increase movement of the dorsal interossei muscles of the hand, increase movement of the volar interossei palmar muscles of the hand, and increase movement of the lumbrical muscles of fingers, as well as many other applications.

2. Description of the Prior Art

Rehabilitation and prevention of median nerve entrapment has generally dealt with wrist angle, body posture, and fatigue, rather than finger movement. Most authors consider the wrist flexion of prime importance. "Within the work place, repetitive wrist flexion and extension and continuous use of the fingers with the wrist either extended or more commonly flexed palmarly are the usual hazards associated with this cumulative trauma disorder syndrome." (23A) pp. 1347 et seq, at 1373.

" . . . intracanal pressure rises with flexion and extension." (24B) at 348. Similarly, subcutaneous cancer prevention, has focused on self examination instruction rather than the ability to tactilely identify a foreign mass. Thus, neither biomechanics of engineering nor medical research has related the health of the finger tips with preservation of the sensory and motor operations of the nerves.

For a subcombination usable together in a single combination, yet distinct and separately useable, see U.S. Pat. No. 6,692,435 issue date 17 Feb. 2004.

2A. Background of the Invention: Keyboards

Communication has always been necessary. By the end of the Second Millennium A.D. keyboards and computers have become ubiquitous, to inform, solve, record, measure, compose, design, entertain and plan. Until the typewriter was invented, all written communication was one handed. The typewriter allowed two handed composition, and an increase in efficiency by an increase in finger flexion.

For a discussion of the QWERTY, Dvorak and efficient keyboard layouts see U.S. Pat. No. 5,352,050, 1996 U.S. Pat. No. 5,498,088.,1872 circa. Sholes created the QWERTY keyboard (based on the left six letters on the third row). According to Beeching, Sholes' ruse was "probably one of the biggest confidence tricks of all time . . . the idea that the so-called 'scientific arrangement' of the keys was designed to give a minimum movement of the hands was, in fact, completely false!" In 1873, the Remington Company bought Sholes' patent for the 'typewriter' and began shipping it in 1874. In 1905 an international conference of typewriter manufacturers and teachers decided the future of print communication. The QWERTY layout was adopted because typing teachers had been teaching QWERTY for decades. According to Beeching: "The battle raged backwards and forwards. Nobody could agree on what a new keyboard should be, but the biggest opposition came from teachers of typing. As it still does today. They wanted things to remain as they were, and they are still the most reluctant to change their methods and learn all over again. All present keyboards are, therefore, based on the 'QWERTY' layout." (5) pg. 40-41.

QWERTY has its critics: "awkward . . . designed to slow typing" (46). "worse possible arrangement" Typists' Speed & Efficiency, by Virginia Russell, Computer Technology Review, Winter 1985; "very poor" Illustrated World Encyclopedia, Vol 14, 1970, Glen Cove, New York, p. 4694; "wrong thing" interview in Conquering the Keyboard, by Robert Alonso, Personal Computing, August 1985, at 72; "costly . . . error . . . slows . . . produces fatigue" U.S. Pat. No. 3,847,263, 1974, col. 1, USPTO; "inefficient" U.S. Pat. No. 4,655,621, 1987, column 1, USPTO; "not the best . . . (makes) much more work" 1994 Compton's Encyclopedia, Typewriter p. 342; and also see "The Case Against QWERTY" at National Museum of American History, Smithsonian Institution, Wash. D.C. circa 1992. As of 1998, QWERTY continues as the standard keyboard layout.

Since Sholes, several inventors have designed keyboards to increase efficiency, increase speed, reduce awkward positions, reduce cramping, avoid rhythm slow down, reduce errors, and reduce fatigue. These include Rowell, Hoke, Dvorak, Bower, Dodds, X, Einbinder, Malt, Menn, Holder, and Diernisse. Recent efforts include:

1991. Key Arrangement and Method of Inputting information from a key arrangement, U.S. Pat. No. 5,003,301. Romberg selects Bower's letters for the home row.

1994. Keyboard Arrangement to maximize typing speed and ease of transition from a Qwerty keyboard. U.S. Pat. No. 5,352,050, 1996 U.S. Pat. No. 5,498,088. Choate places Bower's letters on home row.

1998. Novel Keyboard arrangements and method for increasing typing speed. Application Ser. No. 08/652,109 issuing as U.S. Pat. No. 5,718,590. Choate outlines a method of training.

Although a report on telephone company employees concluded the use of DVORAK versus QWERTY keyboard was not associated significantly with any listed musculoskeletal outcome measures. (22) The methodology of the report was deficient as the questionnaire sampled a small portion of the work force, and did not seek information or compare workmen's compensation claims or absenteeism, even though both statistics were available company wide. "Hadler's analysis of the U.S. West case casts doubt, in his opinion, on occupational causation of these CTDs. He implicated the following locally intrinsic geographic factors which, he felt, accounted for the increased reports and disability in the Denver area: increased worker complaints, psychosocial factors, health services that were more receptive to the work relatedness of complaints, and increased utilization of surgical intervention among physicians in the community." Hadler, N: Arm Pain in the workplace: a small area analysis, J. Occup Med 34(2):113-119, 1992. (53) Hadler noted a significant geographic variation in incidence of CTS (approaching ten fold in four of the U.S. West states). Ibid at 49. The operators reporting the ten fold increase of CTS were in states using QWERTY. (58)

Since Sholes, many efficient layouts have been invented. Each reducing the flexion and travel of the fingers.

2B. Background of the Invention: Health, Median Nerve Entrapment i. Carpal Tunnel Syndrome "Carpal Tunnel syndrome" refers to the compression of the median nerve (due to inflammation of flexor retinaculum, arthritis, or tenosynovitis) as it passes through the osteofibrous carpal tunnel along with the tendons of the long digital muscles which typically results in paresthesia (tingling), anesthesia (loss of tactile sensation), or hypesthesia (diminished sensation) in skin areas related to the thumb, index, middle, and lateral ½ of ring fingers. The palm may be saved due to palmar cutaneous branch arising superficial to flexor retinaculum. A progressive loss of strength and coordination in thumb with diminished use of thumb, index, and middle fingers as nerve is compressed is also common. Carpal Tunnel syndrome is relieved by partial or complete division of the flexor retinaculum." "University of Minnesota researchers estimate between 400,000 and 500,000 carpal tunnel surgery cases occur annually in the United States, with economic costs in excess of $2 billion a year." (52)

Since the early sixties, CTS has been attributed to bent wrists, ("What causes CTS? Work activities and hobbies that keep the wrist bent for a long time, or that require pinching or gripping motions. Examples include: typing or working at a computer keyboard." (15)) and not to finger flexion.

Different keyboard layouts' (to wit: QWERTY, DVORAK and AsInRedHot) permit different tendon movement within the carpal canal.(46) Angular movements of the fingers place greater stress on the carpal tunnel than just simply depressing a key. "While the amount of movement on a particular key is exactly the same in the keyboards we used, the problem is the large number of times you have to go to the top and bottom rows using QWERTY. As soon as you move from the home row, you increase the angular motion of the fingers and sliding motion of the tendons, which increases the potential for CTDs. Our hypothesis was that excessive tendon motion in the carpal canal induces trauma to the nearby tissues. It appears that alternative key location is a good way to reduce finger and tendon motion." (46B) Carpal Tunnel Syndrome (CTS) is caused by swelling of the flexor tendons and compression of the median nerve within the carpal canal. The main structures in close proximity to the median nerve are the finger flexor tendons—Flexor Digitorum Profundus and Superficialis. Thickening of the flexor tendon sheaths, secondary to repetitive motion, has been implicated as a cause for compression of the median nerve (Werner et al. 1983). Cyclic loading tests on the profundus tendons have shown that stress transmitted to the sheath during excursion is significant and a cause of cumulative strain (Goldstein et al 1967). The highly repetitive sliding motion of the tendons through the canal might not only produce tendinitis or tenosynovitis but focal damage to the nerve as well. ((46) p. 195)

The angle data was incorporated into a predictive model developed by Armstrong and Chaffin (1978), which relates the finger and two extrinsic finger flexors, profundus and superficialis, as a pulley system dependent on the joint angle and tendon moment arm. Joint thickness measurements were taken of each subject as described in the Collation of Anthropometry (Garrett et al. 1961). ((46) p. 195.) Total tendon motion for typing on a matched sample on the QWERTY, DVORAK and ASINREDHOT layouts provided results. (Ibid.) Two of three subjects on the DVORAK and ASINREDHOT layouts required less total tendon excursion than typing on the QWERTY layout. (Ibid.)

ii. Conditions for Swelling

Keyboard users afflicted with these disabilities will be helped by the invention in reducing finger extension and flexion, as compared to QWERTY. Besides observing that most CTS sufferers are women, aged 40 to 60, authors have attributed CTS to a wide variety of metabolic and non-metabolic conditions, which are listed below. Causes and sources, or associated metabolic and non-metabolic conditions of CTS listed in (42-26) and (1). For a listing and definition of about a bakers dozen of conditions see U.S. Pat. No. 5,718,590, under help examples.

The pathology includes one or more of the following: aberrant anatomy, acidosis, acromegalic arthritis, acromegaly, acrosclerosis, acute wasting paralysis, acute ascending paralysis, acute anterior poliomyelitis, adenohypophysis, aerobic exercise, aging, alcoholism, amyloidosis, anemia, aneurysms, angina, apoplexy, arachnodactyly, arteriolar disease, arteriosclerosis, arteriovenous malformation, artery, arthritis of rheumatic fever, arthritis, atrophic arthritis, atrophy, backward cardiac failure, baseball finger, Bence-Jones protein, benign tumor, birth palsy, blood vessel, bone marrow, bony ankylosis, brachial plexus, brachial birth palsy, brachial paralysis, brachialgia, brain, brain abscess, Buerger's disease, bulbar apoplexy, burn, bursitis, calcinosis, calcium, calcium deposits, callus, canal volume increased, canal volume decreased, capillary walls, cardiac failure, carpal bones, carpal tunnel syndrome, carpometacarpal joint arthritis, cartilage, cataract, central nervous system, cerebral vessels, cerebral palsy, cervical adenitis, cervical spine arthritis, cervical radiculopathy, Charcot's arthritis, Charcot-Marie-Tooth disorder, chorionitis, chronic arthritis, cigarette smoking, clubbed finger, collagen, coma, congestive, connective tissue, consciousness, contraceptive pills, cretinism, cyst of joint capsule, cyst of semi-lunar cartilage, cystic tumor of tendon sheath, cystic, dactylitis syphilitica, debility, deep palmar retroflexor space abscess, deformity, degenerative joint disease, degenerative conditions, deltoid, demineralization, dermatosclerosis, diabetes, diabetes mellitus, diabetic polyneuropathy, digital neuropathies individual, digital arteries, digits, disuse osteoporosis, dolichostenomelia, dropsy, drumstick finger, dyspnea, dystrophia myotonica, ear, edema, embolism, endocrine organs, eosinophilic cells, epicondylitis, epidemic paralysis, epidermis, Erb-Duchenne syndrome, erythroid myeloma, extracranial lesions, extravasation, fascia, fibromyalgia syndrome, flaccid paralysis, fracture, ganglion, gastric, gastrointestinal, glycosuria, gonococcus, gonorrheal arthritis, gout, gouty tophus, gouty arthritis, granulation, gumma, hammer finger, Haversian spaces, head injury, heart failure, heart, Heberden's arthritis, Heine-Medin's disease, hematogenous arthritis, hematoma, hemic myeloma, hemodialysis, hemolytic streptococcus, hemophilic arthritis, hemorrhage, hereditary conditions, high blood pressure, Hippocratic finger, hunger, hydrostatic pressure, hypercalcemia, hyperemia, hyperesthesia, hyperfunction, hyperglobulinemia, hyperglycemia, hypermotility, hyperplasia, hypertension, hypertrophic pulmonary osteoarthropathy, hypertropyhic reaction, hypothyroidism, incoordination, infantile paralysis, infection, infectious arthritis, infectious conditions, inflammation, inflammatory conditions, insulin, intracranial lesions, ischemic paralysis, joint capsule, joint surface, Kahler's disease, ketosis, Klumpke palsy, knuckle, lead palsy, leprosy, lesion, leukocytosis, lipoma, lock finger, luxation, lymph, lymphocytic myeloma, lymphoid myeloma, malignant, mallet finger, malnutrition osteoporosis, Marfan's syndrome, marrow, mass lesion, median nerve entrapment, medulla oblongata, menopausal arthritis, menopause, menstruation, metabolic, migraines, mucoid hyaluronic acid, mucopolysaccharidosis, multiple sclerosis, muscle spasms, muscle tenderness, muscular dystrophy, myelocytic sarcoma, myeloid myeloma, myeloid tumor, myeloma, myeloma multiple, myofascial dysfunction, myosclerosis, myotonia dystrophica, myotonic dystrophy, myxedema, neoplastic conditions, neuritis, neurological, neurons, neuropathic arthritis, neuropathies individual, neurotrophic arthritis, obesity, obstetric paralysis, osmotic pressure, ossification, osteoarthritis, osteoporosis, palsy, paralysis, paralytic poliomyelitis, phalangectomy, phalangitis, phalangitis syphilitica, phalangization, phalangophalangeal amputation, phalanx, phosphatase, phosphorus, plasma, plasma cell myeloma, plasmacytes, plasmacytic myeloma, plasmacytic sarcoma, plasmacytoma, plasmocytic sarcoma, plasmocytic myeloma, plasmocytoma, plasmona, pneumococcus, polio, poliomyelitis polyneuritis, pons, postinjury, postmenopausal osteoporosis, power grip, pregnancy, prenatal syphilis, printer's palsy, proliferative arthritis, pronator syndrome, protein concentration, proximal lumbrical insertion, proximal median neuropathy, psychosis of hysterical numbness and clenched-fist syndrome, pulmonary, punctiform, Quervain's disease, Quinquaud's phenomenon, radiation neuritis, radiohumeral articulation, radiohumeral bursitis, radiohumeral epicondylitis, Raynaud's syndrome, Recklinghausen's disease, reflex sympathetic dystrophy, renal failure, respiratory, reticular fibers, rheumatic fever, rheumatoid arthritis, rheumatoid tenosynovitis, ruptured disk, sanguineous apoplexy, scarlatinal synovitis, scarlatinal arthritis, scarlet fever, scleriasis, scleroderma, seal finger, seizures idiopathic peripheral causes, senile, osteoporosis, senility, skeleton, sodium urate, spastic diplegia, spider finger, spinal nerves, spinal cord, spinal cord lesions, splanchnomegaly, sprain fracture, springfinger, Steinert's disease, stellate cells, stroke, subchondral spaces, subdural hematoma, sugar tolerance, swallow, swelling, symmetrical synovitis, syndactyly, synovectomy, synovial, synovial tissues, synovial distention, synovial proliferation nonspecific, synovitis, synovium nonspecific fibrosis, syphilitic arthritis, syringomyelia, systemic disease, tabes dorsalis, tactile anesthesia, tendinitis, tendon sheath, tendons, tendovaginitis stenosans, tenosynovitis, thirst, thoracic outlet syndrome, thrombosed, thrombosis, thyroid hormone, thyroid conditions, tophaceous gout, trabeculae, transient ischemic attacks, trauma, traumatic conditions, tremors, trigger finger, tuberculosis, tuberculous tenosynovitis, tuberous sclerosis, tumor, tumor benign, ulnar nerve neuropathy, uremia, uric acid, urine, vascular spasm, vascular conditions, vasculitis, vasomotor disturbances, viscera, Volkmann's paralysis, weakness, webbed fingers, weeping sinew, weight, white-finger syndrome, or wrist malalignment.

iii. Tendons at Work

1. Carpal tunnel syndrome (herein also "CTS") among computer keyboard users stems from the original design of the QWERTY keyboard. "In the industrial setting, certain jobs that require repetitive flexion, extension, or deviation of the wrist have been associated with the symptoms of carpal tunnel syndrome . . . computer keyboard work . . . " (24B) CTS is a subclass of cumulative trauma disorders (CTDs). For a survey of the medical literature, see (53).

Carpal tunnel syndrome is caused when membranes of tendons in the carpal tunnel of the forearm and hand thicken and press nerve up against the bones. "Carpal tunnel syndrome (CTS), a painful disorder of the wrist and hand, has lately been the subject of much publicity and even litigation, when injured workers have taken employers to court. CTS is one of many injuries caused by repeated strain, such as that produced by working long hours at a computer, and it's on the rise. Thousands of cases are diagnosed each year. . . . Deriving its name from the Greek karpos, or wrist, the carpal tunnel is the passageway, composed of bone and ligament, through which a major nerve system of the forearm passes into the hand. The carpal tunnel is like a cable for the median nerve and nine tendons. The nerve supplies sensation and controls the muscles in part of the hand, and the tendons allow the fingers to flex. The wear and tear of repeated movement may thicken the lubricating membrane of the tendons, increasing pressure inside the carpal tunnel and pressing the nerve up against the bone. This process, called nerve entrapment, can be caused not only by repetitive strain, but by bone dislocation or fracture, arthritis, diabetes, or fluid retention (as may occur in pregnancy)—anything that narrows the tunnel and compresses the nerve and tendons." (3). "As . . . fingers are flexed or extended, the tendons and the median nerve within the carpal canal must be able to glide relative to the canal as well as to each other." (42-26). Repetitive trauma overwhelms a tissue's ability to repair itself.(9A) Repetitive Digit flexion causes swelling of tendons. "Repetitive digital flexion in an individual unaccustomed to such activity can induce significant tenosynovitis of the digital flexors." (8A)

The carpal tunnel has a roof of the transverse carpal ligament, to contain the tendons of flexor pollicis longus, flexor digitorum superficialis, and flexor digitorum profundus, the median nerve and artery.(24B) The swelling of these tissues presses the median nerve against this roof. "The median nerve, the softest and most volar structure in the carpal canal, is brought against the transverse carpal ligament, especially when there is forceful digital flexion with simultaneous wrist flexion. The nine long flexor tendons, when tensed, compress the median nerve against this ligament." (12) at p. 235.

2. Carpal Tunnel Syndrome is the name ("Moersch coined the name of the syndrome in 1938." 23B) for the symptoms of median nerve entrapment. Also called the three and a half finger disease, median nerve neuropathy, compression nerve injury, repetitive motion disorder, occupational overuse syndrome, repetitive strain injury, cumulative trauma disorder, dynamic carpal tunnel syndrome. Ibid at 23B) In which the thumb, index, middle and half of ring fingers have tingling and numbness. Paresthesia or dysesthesia of radial 3½ fingers.(7) Pressure on the median nerve occurs within the carpal tunnel. Nine flexor tendons, the median artery, and carpal ligament, are the structures adjacent to the median nerve. These swelling tissues press the median nerve. "Increased bulk may result in median nerve compromise at the . . . flexor digitorum sublimis". (9A) at 231. Injury to the tendons leads to inflammation. " . . . accumulated injury to . . . tendons, . . . leading to inflammation . . . " 1986 National Institute for Occupational Safety and Health (NIOSH) report cited in (53) at 48. Flexing tendons can aggravate inflammation causing tendon sheaths to swell. Tendons can hypertrophy, (21A, 21B. 21C) and swelling can be seen in the forearm above the wrist creases. "The swelling is visualized just proximal to the wrist flexion creases because of the unyielding transverse carpal ligament. Pain aggravated by finger motion can be reported all along the volar surface of the forearm. Median nerve compression can also occur and produce severe pain." (8A)

Among others, two possible reasons why repetitive finger flexion aggravates carpal tunnel syndrome are: The first is tendon excursion irritates and inflames the synovial sheaf to cause swelling (tenosynovitis). "Compression of the median nerve within the carpal tunnel can be attributed to . . . an increase in volume of tunnel contents secondary to tenosynovitis, or thickening of the transverse carpal ligament." (26E) "Most of (CTS) cases probably are caused by nonspecific tenosynovitis of the flexor tendons." (24A) (Also described as the hypertrophy or edema of the synovium of the transverse carpal ligament), (24B). The second is due to exercise, the tendons themselves hypertrophy.

iv. Wrist flexion or Finger Flexion

The University of California, Berkeley, health letter proposes that repeated finger movement promotes nerve entrapment. "The carpal tunnel is like a cable for the median nerve and nine tendons. The nerve supplies sensation and controls the muscles in part of the hand, and the tendons allow the fingers to flex. The wear and tear of repeated movement may thicken the lubricating membrane of the tendons, increasing pressure inside the carpal tunnel and pressing the nerve up against the bone. This process, called nerve entrapment, can be caused not only by repetitive strain, but by . . . anything that narrows the tunnel and compresses the nerve and tendons." (3) "Repetitive wrist/finger movement with loading of the tendons in the carpal tunnel;" is one of six major occupational factors for CTS. Silverstein B A: Fine L J, Armstrong T J: Carpal tunnel syndrome: causes and a preventative strategy, Semin Occup Med 1:213-21, 1986. Cited in (53), at 50. Finger movements with a flexed wrist can cause tendons in the carpal tunnel to be displaced against adjacent walls, causing eventual inflammation, swelling, and median nerve compression. Armstrong T J: An ergonomic guide to carpal tunnel syndrome, Akron, 1983, American Industrial Hygiene Association. Cited Ibid. This invention will test whether the same inflammation and swelling can be induced without a "flexed wrist."

See CTS research for swelling.(53) A swollen tendon can press the median nerve. "Conditions that increase the volume contained within the carpal tunnel, such as a swollen tendon or muscle anomaly, or decrease the area of the tunnel, as after a fracture, can increase CT pressure and compress the only structure with elasticity in the canal—the median nerve." Ibid (53) at 53. Some CTS patients relate subjective feelings of swelling, although there may be no apparent swelling on examination.(54) Hands swell after hand stress testing. "Braun et al. studied provocative stress testing in 40 patients which they diagnosed as having "dynamic CTS." These patients had transient symptoms which occurred with stressful activity and resolved with rest or elevation. Hand volume (by a standardized water displacement method) and monofilament testing were examined before and after hand stress testing. . . . Hand swelling was documented in 34 patients after stress testing, with 17 of theses accompanied by quantitative sensory loss." (55)

Overuse syndromes result from repetitive loading episodes at a force or elongation level well within the physiologic range.(8A)

Preventing carpal tunnel syndrome is better, than the repeated treatment of the syndrome by release of the deep transverse carpal ligament. "As carpal tunnel syndrome becomes increasingly recognized in the work place as a repetitive trauma or cumulative trauma syndrome, it seems more and more certain that modification of the work environment by redistribution of work mechanics, modification of tools and handles to be more compatible with hand function, and the attention of biomechanical engineering designed to protect the worker will create a focus on the prevention of this syndrome, rather than the repeated treatment of the syndrome by release of the deep transverse carpal ligament. An important part of the evaluation of industrial biomechanics will be the evaluation of the employee prior to assumption of a position in the work place, combined with a knowledge of the amount of stress applied to the worker's hands in a particular working environment. It should then be possible, through knowing the stress to which the worker is exposed in doing a specific job and that worker's capacity for stress, to provide a suitable match of the worker's abilities with the job requirement and thereby, hopefully, to reduce the incidence of cumulative trauma or stress related carpal tunnel syndrome."(23B)

Evidence is moving toward acceptance of workplace factors in the etiology of carpal tunnel syndrome, but clear proof, as well as "dose-response curve," the amount of repetitive motion required to cause carpal tunnel syndrome, is not available. (1) at 1377.

Repetitive motion and carpal tunnel syndrome are described: "Work-related forceful repetitive motion contributes to (CTS)"(56); "work-related repetitive motion is only one of many factors that can aggravate (CTS)"; Colorado orthopedic surgeon Willard Schuler, M.D. quoted. (42-32) "Working on a keyboard all day can put you at (risk of RSI)". (57)

v. The body is all one piece. Upper extremity nerve pathology includes one or more of the following: reduced flexion and extension, in, on or about, at least one of the abductor, elbow, extensor tendon, finger, fingernails, flexor retinaculum, flexor tendon, flexor superficialis muscle, forearm, hand, humerus, interosseous muscles, ligament carpal dorsale, long flexor muscle, median artery, median nerve, middle phalanx, middle finger, palm, palmaris brevis, palmaris longus, palmaris longus tendon, periarticular tissue, phalangeal joints, radial nerve, thumb, transverse carpal ligament, or wrist.

2C. Background of the Invention: Health, Oncology

Chronic repetitive digital flexion injures the median nerve. "Digital flexor tenosynovitis at the wrist commonly causes signs and symptoms of carpal tunnel syndrome . . . This condition may occur after a hyperextension injury to the wrist or after chronic repetitive digital flexion." p. 97. (7) The flexor tendons have the central role for median nerve entrapment. "Phalen reported that the most common cause of carpal tunnel syndrome was fibrosis or thickening of the flexor synovium secondary to a chronic, nonspecific tenosynovitis of the flexor tendons in the carpal tunnel." (26E) The position of the center of pressure is highly correlated to the relative positions of the nerve and the tendons.

Conservative treatments for pain from the median nerve include wrist splints, and changing jobs. But what of the rest who can't change jobs, or for whom wrist splints aggravate their condition? Left untreated, a compressed nerve will cause atrophy to the muscles which it innervates. Hence, CTS cases not responding to conservative treatment receive surgery, i.e. sectioning the transverse carpal ligament. Complications of this surgery include scarring, incomplete release, laceration, tendon adhesion, and lack of grip strength recovery. (24B) at 352. Complications include fracture, injury to nerves, neuropraxis, transection of the nerve, injury to artery, injury to palmer arch, hematoma, infection, and reflex sympathetic dystrophy at a rate of between two tenths and twelve percent.(24C) Despite the complications, carpel tunnel release is the most frequent hand and wrist surgery performed in the United States, " . . . approximately 463,673 carpal tunnel releases performed annually in the United States . . . " (24D)

"University of Minnesota researchers estimate between 400,000 and 500,000 carpal tunnel surgery cases occur annually in the United States, with economic costs in excess of $2 billion a year . . . " (52), with a 15 to 20 percent failure rate, (1) at 1376, and ten percent inappropriate procedure rate.(28) Because of the vast numbers of people involved, the totally disabilitating nature of the disease, the indispensable part of the body which is affected, and its seeming imperviousness to prevention, CTS rivals arthritis and exceeds polio for the harm it is causing America. Carpal Tunnel Syndrome is the "PC polio" of the nineties.

There are 40,000 carpal release surgeries each month in the United States; it is the #1 hand operation. These surgeries are supposed to be stage 3 carpal tunnel syndrome, meaning loss of sensation from the median nerve, tingling or pain to the hands and fingertips, both day and night; patients also suffer numbness in the finger tips, have trouble picking up coins, turning keys, and doing fine motor tasks. Eighty percent of the carpal tunnel syndrome cases are women, so probably the vast majority of the release surgeries are on women. Eighty percent of 40,000 indicates there may be 32,000 women with stage 3 having surgery operations every month. Further injury to the median nerve resulting from the carpal release surgeries ranges from 0.2 to 12%. Thus, between 64 to 4,000 women per month have their nerves further injured in wrist surgery.

Breast cancer and carpal tunnel syndrome are female gender diseases, in that the majority of cases are female. There are no known means of preventing breast cancer. (Cancer Nursing, October '87, 385). One in nine women develop breast cancer in their lifetime, thus 6 to 400 of the monthly nerve injured women patients are at risk to develop breast cancer in their lifetime. The same reasoning can apply to arthritis, leprosy, scleroderma, or any thing that ruins sense of touch.

Breast self exam (BSE) is the first and best defense to the early detection of breast cancer; the goal is to detect the mass before it spreads (metastasizes). This is best accomplished by regular monthly tactile self examinations. BSE is free and convenient, as compared to clinical breast examination (CBE) by a physician or mammography. Early detection results in very favorable treatment and recovery statistics. Yet, studies also show that half of the breast cancer cases are discovered only after the mass has spread. The principle is if there is a small enough mass, and a large enough tactile deficit, a patient with advanced carpal tunnel syndrome, attempting to palpate the mass, may miss the feel of a lump of cancer. Why are half the cases discovered late? Either women don't check, don't care, or can't feel. If they check and care, but can't feel, they may miss a mass. If their tactile sense has been compromised, they are at greater risk for delayed discovery of the mass, and more likely to have a poor prognosis for recovery.

A similar conclusion applies to vulvar and testicular self examination. If the tactile deficit is great enough, and the mass small enough, the mass will be missed.

Carpal tunnel syndrome, an upper extremity ailment,(24A is associated with reduced sensation in the hand as measured by grip strength and tactile sensitivity, with reduced flexion strength, and with slow reaction time.

3. Objects of the Invention

It is an object of the present invention to provide a method for testing a device which will prolong the onset of symptoms for a person having upper extremity nerve pathology, the method comprising the steps of:

providing the person with a device, instructing the person on the proper use of the device, as determined by the manufacturer or creator, establishing a base line data for the person, monitoring the person so the use is consistent with the instructions, measuring changes in the person's symptoms, having use of a second, different device, repeating the previous steps with at least one different device, comparing the results of monitoring use and measuring changes to determine a preferred device selecting a device which prolongs the onset of symptoms of nerve pathology.

Another object of the invention is to establish a new use for all devices or products that improve the prognosis for treatment of the 150 different metabolic and non metabolic conditions that are precursors for carpal tunnel syndrome, by prolonging the onset of symptoms and improving tactile sensation.

Another object of the invention is to find a new use for the efficient keyboard, in which the use of the keyboard reduces finger flexion, by establishing use of efficient keyboards prolong the onset of symptoms of median nerve entrapment.

Another object of the invention is to establish a method for testing and preventing the onset of symptoms of nerve pathology, wherein the structures adjacent to the nerve include the nine flexor tendons next to the median nerve.

Another object of the invention is to establish a method for testing and preventing the onset of symptoms of nerve pathology, wherein the work of the nine flexor muscles next to the median nerve is shifted to the lumbricals of the fingers, the dorsal interossei of the hand, the volar (aka palmar) interossei muscles.

Another object of the invention is to establish a method for testing "dose-response curve," the amount of repetitive motion required to cause carpal tunnel syndrome.

Another object of the invention is to establish a new use for all devices or products that reduce inflammation to the median nerve, by improving the discovery of cancer mass by subcutaneous self examination by increasing tactile sensation by decreasing median nerve entrapment.

Another object of the invention is to establish a method for testing a person, having upper extremity nerve pathology, in order to determine a device which will advance the earlier detection of subcutaneous masses, including maladies, by self examination, the method comprising the steps of:

providing a person with a device demonstrated to prolong the onset of symptoms of nerve pathology, instructing the person on the proper use of the device, as determined by the manufacturer or creator, monitoring the person so the use is consistent with the instructions, instructing the person in detecting typical masses by finger and hand palpating through a opaque cover, establishing a base line data for the person and onset time duration for operating the device, measuring changes in the person's symptoms, repeating the previous steps with at least one different device, comparing the results of monitoring use and measuring changes to determine a preferred device, obtaining a dose response, instructing person to use device for less than duration required to achieve dose response, instructing the person in preserving and improving the tactile sensation of the hand and finger tips for self examination.

Another object of the invention is to establish a method for testing devices or products that reduce inflammation to the median nerve.

SUMMARY OF THE INVENTION

In accordance with the foregoing objectives, there is provided a means to test a device as to whether its use prolongs the onset of symptoms of median nerve entrapment. The test requires a controlled study.

In another preferred embodiment of the present invention there is the use for the keyboards that reduce finger flexion in that they prevent the onset of symptoms of carpal tunnel syndrome.

In another preferred embodiment of the present invention there is the use for the keyboards that reduce finger flexion in that they are therapeutic in palpation and early detection and preventive treatment of subcutaneous cancers.

In another preferred embodiment of the present invention there is the use for anti-inflammatory chemicals, drugs and agents which prevent the onset of symptoms of carpal tunnel syndrome and are therapeutic in palpation and early detection and preventive treatment of subcutaneous cancers.

In another preferred embodiment the present invention protects the carpals from stress injury. The carpals are 8 wrist bones. There are 17 tendons in the wrist. Tenosynovitis is an inflammation of the tendon sheaths. There are 9 major nerves, arteries and veins in the wrist. There are also several sheaths and ligaments in the wrist. By reducing the amount of stress and work that the fingers, hands, wrists, etc. must perform during typing, the present invention can drastically reduce the incidence of injury associated with typing using the QWERTY keyboard.

In another preferred embodiment, the present invention replaces the work of the finger flexors and extensors with the work of the lumbrical and interossei muscles, thereby reducing tendon excursion and prolonging the onset of symptoms of carpal tunnel syndrome.

In another preferred embodiment, the present invention divines a means so devices can be tested as medical devices which are therapeutic for carpal tunnel syndrome and ten dozen other upper extremity disorders.

In another preferred embodiment, the present invention identifies a co-morbidity between CTS and breast cancer, in that women using breast self examination suffer reduced tactile sensation in their finger tips when they have CTS or have had carpal tunnel release surgery followed by complications.

In another preferred embodiment, the present invention tests a variety of devices to determine a preferred device for a user, wherein the preferred device has desired attribute to delay onset of the symptoms for that user.

BRIEF DESCRIPTION OF THE DRAWINGS

FIG. 1 illustrates the Table including data on testing device for prolonging onset of symptoms of nerve pathology caused by an upper extremity malady.

DESCRIPTION OF THE PREFERRED EMBODIMENT

"As in Red Hot" is an anagram from the 10 most used letters in English. QWERTY keyboard increases the symptoms of a medical disability termed "Carpal Tunnel Syndrome," which is also wrist injury.

This invention tests whether flexion required by typing with the QWERTY layout accelerates or aggravates the swelling of tendons and the entrapping of the median nerve.

A. Purpose of the Invention

The purpose of the invention is to evaluate two keyboard layouts for carpal tunnel syndrome therapy, and to see if the efficient keyboard will be used as an adjunctive tool to other treatments or therapy for CTS for typists.

After evaluation of results from different sensory tests, questionnaires, and clinical examination, the final test invention consists of a medical history,(8C) 2 simple tests describing the subjective assessment of pain by the subject (visual analogue scale/verbal rating scale, and hand diagram), diagnostic tests include 2 motor function tests, (ability to turn door knob and turn key, and picking up small objects or coins that are dropped on the table), 1 symptomatic question to add to the medical history (paresthesia in the hand or fingers, especially at night), and 1 clinical measurement (nerve conduction velocity, median and ulnar nerve, and motor and sensory—orthodromic.), 3 clinical measurements (Phalen's test, Tinel's sign, water volume/caliper/tape measure), 2 activity tests requiring the hand to transmit force to a tool (typing on different keyboard layouts—QWERTY and AsInRedHot), and post activity tests measuring change in pain and swelling (water volume, pain, and sensory ability). Each selected test has a history of evaluation.

If a patient is without constant symptoms (pain, swelling, tingling), can a patient still have CTS? Yes, because symptoms may require activity for the inflammation to occur. The subject need not be in constant pain, to either have CTS or be selected for the typing test. The assumption is that if the subject has been diagnosed for CTS, digit repetitive flexion (i.e. typing) will make the pain appear.

The typing exercise is not known to be a finger exercise to relieve symptoms, such as the shaking of a hand is sometimes used to relieve symptoms. Typing, even on an efficient keyboard, is not expected to be a treatment for CTS to relieve symptoms (i.e. if a little is good, a lot is better).

The invention uses of this efficient keyboard to prevent onset of swelling for a greater amount of hours during typing than typing on a QWERTY layout keyboard.

The medical history is used to take out subjects who have arthritis or current pregnancy from the typing exercise.

B. Management or Effectiveness Trial: Generalize Procedure or Treatment to Practice.

Sensory Tests:

This test invention, for carpal tunnel syndrome, will evaluate the following parameters: subjective opinion about pain and discomfort, objective sensory stability of the median nerve, and swelling of tissue after the typing activity, sensory stability of the ulnar nerve, and motor and sensory conditions.

The medical literature (32 articles) lists 67 tests that are suitable for the carpal tunnel syndrome part of the invention. In addition, words from typing lessons are included for the typing activity evaluation. (27)

The test battery is performed with each subject in the subject group.

C. Diagnostic Tests.

Nine diagnostic tests are selected. They are Water Displacement, Caliper, Tape Measure for swelling; Phalen's Test, Tinel's Sign for numbness and tingling; self report analogue scale, self report hand diagram for subject's pain perception; dropping object, turn door knob and key for motor function; nerve conduction velocity (NCV) tests for median and ulnar nerve abnormality and distal sensory latency, distal motor latency and conduction velocity. 58 other tests were evaluated but not selected. They are unnecessary in order to keep the evaluation manageable for subject and investigator. Criterion for abandonment include tests that were invasive, and tests that focused on hand structures outside the carpal canal.

D. The Explanatory Trial—Activity (AsInRedHot) Produces Better Results than Activity (QWERTY)

i. Invention: Typing Repetition with QWERTY.

All subjects will be asked to type until they feel pain, or for four hours. After typing, they will then report on the visual analogue scale and be measured by the water displacement test.

Before the interview and tests, the subjects will be requested to avoid, for twenty four hours prior to the test, any activity, especially typing, that requires substantial force from the hands, to avoid non-clinical inflammation or swelling. The subjects are also asked to avoid pain killers or medication before the typing test, as these may mask the pain from the median nerve entrapment, if any. In any case, the subjects will also be asked, as individuals, to follow the same daily routine and similar activities before each typing test.

In each test, the subject, after first taking the medical history and sensory tests, will then be instructed to practice the typing test for 3 to 5 minutes, or such longer time, in order to become familiar with the testing system, and be able to type at similar speeds on both boards. Then, under verbal encouragement, the test will be performed, and the result is recorded by the investigator.

In this part of the study a typing test is administered. The subject is asked to type with 8 fingers and 2 thumbs as many times as possible (maximal effort) to measure the number of flexions it takes to cause discomfort, to fatigue the muscles and to swell (29) the hand and forearm. The subject is allowed to change positions, sit or stand, with arms in a comfortable position. In case of lost or mistaken words, the subject is to ignore the errors and to continue the performance. The number of words is measured by dividing keystrokes by 5. The keystrokes are recorded with an electronic counting device (computer program). The fixed keyboard style demands from the fingers a minimum of (½ or ¾ inch) of free movement between center of key caps. The test is performed analogically to normal typing conditions in order to measure the fatigue and swelling of the tissues.

Save the keystrokes to a file for later examination to compare speed and accuracy during the test. The beginning and ending time is recorded by the investigator, or by the computer program. Time can by kept manually with a clock or stopwatch.

Temperature will be maintained at a comfortable level.

In order to control for wrist angle, every typing subject will wear a wrist support or use a wrist pad.

D. ii. Part 2 of Invention: Typing Repetition with AsInRedHot.

The subject will then be scheduled to return after any swelling has gone down to baseline. The invention will be repeated on a similar keyboard with only the letters rearranged. On the AsInRedHot keyboard, pressing the D and E requires minimal flexion, as pressing the middle and index finger on the home row communicates the letters. The Ordinals letters (A D E H I L N O R S T) on AsInRedHot has 0 flexions. The four words "As In Red Hot" on AsInRedHot keyboard has 0 flexions of the fingers, and 2 abductions and 2 adductions, 1 each for left and right index fingers.

E. Subject Inclusion and Exclusion (Escape and Dropout) criteria

The syndrome is more frequent in females (27) by a ratio of more than 2 to 1, and half of the cases occur in subjects between 40 and 60 years of age.(23B) The inclusion criteria for the invention are any adults who type, and who have carpal tunnel syndrome.

Subjects to exclude in various studies will be those who are unable or unwilling to have inflammation symptoms identified. Usual symptoms are weakness or clumsiness in the hand, hypesthesia or paresthesia in the distribution of the median nerve, aggravation of the symptom when using hand (especially typing), numbness in the fingers after sleep, pain in the wrist or distal forearm, shoulder pain, upper arm pain. (23B)

Carpal Tunnel Syndrome is classified into three groups according to the severity of the symptoms.

Early stage injury is defined as symptoms which appear only when provoked and related to specific activities. Symptoms are mainly sensory without motor involvement.

Progressive stage injury is defined as symptoms which are more advanced, and which disturb daily functioning. Motor weakness begins to occur in the affected hand. The subject awakens at night. This is usually when subjects seek medical assistance.

Late stage injury includes having symptoms for many years, with moderate muscle weakness including thenar muscle atrophy. Subjects may report that intolerable conditions are somewhat better, not that the condition is improving, but that the permanent median nerve damage has resulted. Subjects may become asymptomatic to pain and tingling, but persistent numbness indicates permanent nerve damage.(2)

Treatment for temporary Early and Progressive (i.e. pregnancy CTS) stage CTS is usually nonoperative. "25 percent of patients who are pregnant may have symptoms of (CTS)." (18A)

Subjects in the trial, will be under similar therapy, if any, in order to minimize confounding differences.

Exclusions: The invention tests typists that flex their fingers to type letters off of the home row. Hunt and peck typists, who move their forearms and use only two or four fingers, do not sustain the digit flexion of the touch typist. Therefore, subjects will be excluded who do not flex their fingers or use all eight fingers to press the keys, (i.e. exclude people using only the index II or index II and middle III fingers for typing).

As this invention tests the dosage of typing required to elicit a flare up of symptoms (pain and swelling) among different keyboard layouts, those who do not have carpel tunnel syndrome, will be tested separately. We test separately those who have carpel tunnel syndrome Late stage, and whose median nerve is so damaged so that the fingers and hands are numb, without pain. All subjects not completing the study will be asked why they withdrew.

All subjects can be tested on tactile sensation, and to discern whether further injury can result with digit flexion, when pain cannot signal termination of the activity.

F. Blinding, Sample Size and Endpoints.

The endpoints, and what constitutes a success or failure, in a comparison study of QWERTY to AsInRedHot keyboards are based on time, work, swelling, and feedback to pain.

G. Data of the Test Baseline Assessment.

Basic data on the subjects will be obtained from the medical history, or medical records. If available, nutrition history will be considered.

Base Line—Upon the subject's return to any typing test session, the pain, water volume (or thermography) and environment of the study will be duplicated as closely as reasonable to the first session, so each test will be comparable, except for the keyboard layout and subject.

H. Statistics and Assess the Outcomes to Establish which of the Studied Therapies Does the Greatest Good.

The data will be analyzed by calculations, including standard deviation, and a medical history.

I. Medical History.

A limited medical history is used to identify level of therapy, general health, and reasons the person should not be tested.

References Cited in Specification

1. Carpal Tunnel Syndrome, A Practical Review, Katz il v49:6 American Family Physician May 1 '94 p1371(11) infotrac & library
2. Endoscopic Carpal Tunnel Release by Chow in Arthroscopic Surgery, The Wrist, Whipple Ed. J. P. Lippincott Co. Philadelphia, 157 et seq.
3. CTS: relief at hand, School of Public Health, Vol. 11:4, UC Berkeley Wellness Letter, January 1995, p. 7.
5. Century of the Typewriter, by Beeching, Director, British Typewriter Museum, St. Martin's Press: New York, 1974, 28-43.
6. 1994 Compton's Encyclopedia & fact-Index, Typewriter, at 342.
7. Sports-related Extra articular Wrist Syndrome by Wood and Dobyns, in Clinical Orthopaedics and Related Research, by Urist, Number 202, J. P. Lippincott Co. Philadelphia, January 1986, pp. 93-102.
8A. Upper Extremity Tendinitis and Overuse Syndromes in the Athlete, by Kiefhaber and Stern, in Injuries of the Hand and Wrist, in Clinics In Sports Medicine, Vol. 11:1, January 1992, Saunders Co. Harcourt Brace Jovanovich, 39 et seq.
8C. The Preparticipation Fitness Test, by Van Handel, in Overuse Injuries, Clinics In Sports Medicine, Vol. 10:1, January 1991, Saunders Co., p. 3 et seq.
9A. Introduction to Overuse Injuries, By Herring and Nilson, in Clinics In Sports Medicine, Vol. 6:2, April 1987, Saunders Co. Harcourt Brace Jovanovich, p. 225 et seq.
12. The Hand, Surgical and Non-surgical Treatment, by Kilgore and Graham, Lea & Febiger, Philadelphia, 1977. "Nerves" pp. 211 et seq.
15. Carpal Tunnel Syndrome, The Johns Hopkins Medical Handbook, The 100 Major medical Disorders of People Over the Age of 50, by Margolis and Moses, Ed. The Johns Hopkins Medical Letter Health After 50, Rebus, N.Y., 382.
18A. Neurology, Medical Library Lawyers Edition, by Ausman and Snyder, 6:105F, 1990.
21A. "Tendon hypertrophy is associated with increased hydroxylation of nonhelical lysine residues in two specific cross-linking sites in type 1 collagen" by Gerriets and Curwin, in I. Biol Chem (United States) Dec. 5, 1993 268(34) p25553-60. Medline p. 2.
21B. "Echographic assessment of the hand" by Bottinelli, et al, in Radiol Med (Torino, Italy), May 1993, 85 (5 Suppl 1) p227-36, Medline p.3.
21C. "Multiple ruptures of flexor tendons due to hypertrophic change at the distal radio-ulnar joint. A case report." by Minami, Ogino and Tohyama, in J. Bone Joint Surg (Am) (United States) February 1989, 71(2), p.300-2.
22. Comparative Effects of QUERTY (sic) and DVORAK Keyboards in the NIOSH Health Hazard Evaluation at US West Communications, by Hales and Sauter, NIOSH, Cincinnati Ohio, circa 1995.
23B. Entrapment and Compression Neuropathies, by Eversmann, in Operative Hand Surgery, by Green Editor, 3d Edition, Vol. 2, Churchill Livingstone, New York, pp. 1346 et seq.
24A. Clinical Diagnosis of Peripheral Nerve Compression in the Upper Extremity, by Anto and Aradhya, in The Orthopedic Clinics of North America Peripheral Nerve Compressions of the Upper Extremity, George, Ed. 27:2: April 1996, W.B. Saunders, Philadelphia, 227 et seq.
24B. Carpal Tunnel Syndrome by Kulick, in The Orthopedic Clinics of North America Peripheral Nerve Compressions of the Upper Extremity, George, Ed. 27:2: April 1996, W.B. Saunders, Philadelphia, 345 et seq.
24C. Newer Techniques of Carpal Tunnel Release, by Mirza and King, in The Orthopedic Clinics of North America Peripheral Nerve Compressions of the Upper Extremity, George, Ed. 27:2: April 1996, W.B. Saunders, Philadelphia, 355 et seq. Tables 1 and 2, at 363 and 365.
24D. Pitfalls of Endoscopic Carpal Tunnel Release by Einhorn and Leddy, in The Orthopedic Clinics of North America Peripheral Nerve Compressions of the Upper Extremity, George, Ed. 27:2: April 1996, W. B. Saunders, Philadelphia, 373 et seq.
26A. Essential elements of an upper extremity assessment battery, by Fess in Rehabilitation of the Hand Surgery and Therapy by Hunter et al Ed. 3d Ed. 1990, C. V. Mosby, St. Louis. 53 et seq. (splint and rehab forms)
26E. Therapist's Management of carpal tunnel syndrome, by Baxter-Petralia, in Rehabilitation of the Hand Surgery and Therapy by Hunter et al Ed. 3d Ed. 1990, C. V. Mosby, St. Louis. 640 et seq. at 640.
27. Carpal Tunnel Syndrome in Complete Guide to Sports Injuries by Griffith, at 380.
28. Surgical and Diagnostic Procedures: Inappropriate Procedures: 1991 and 1992, Statistical Record of Health and Medicine, by Dorgan Ed. Gale Research, International Thomson Publishing, New York, 1995, p. 183, table 239.
29. Carpal Tunnel Syndrome, Arm and Leg Surgery, The Surgery Book, 73 Most Common Operations, by Youngson, Diagram Group, St. Martins Press, 1993, p. 176 et seq.
42-8. Lane, Merritt, Nathan: CTS: The workup. Patient Care April 15, 1993, pp 97-108, Infotrac, management techniques, pp. 111, Morton L. Kasdan, Connie Lane, Wyndell H. Merritt and Peter A. Nathan, Infotrac
42-26. When to suspect—and diagnosis. (Carpal Tunnel Syndrome) by McCue and Mayer il v33 Consultant December '93 p40(4), copyright 1993 Cliggott Publishing Company. Infotrac, Health Reference Center * May '93-May '96.
42-32. Dissecting the CTS debate. (carpal tunnel syndrome) by Susannah Zak, Figura il v57 Occupational Hazards November '95 p28(4)
44A Management of a patient with lacerations of the tendons of the extensor digitorum and extensor indicis muscles to the index finger. by Kenneth R. Flowers, Philip W. McClure and Christine McFadden il v76 Physical Therapy January '96 p61(6). Copyright 1996 American Physical Therapy Association Inc.
46. Quantification of Tendon Excursion through Kinematic Analysis of Typing Movements on Alternative Keyboard Layouts, by Flannery, Robertson, and Cooper, in Conference Proceedings 19th Anual Meeting of the American Society of Biomechanics, Stanford University California, August 1995, pp.195-196, and sponsored in part by NASA and the Department of Veterans Affairs, with partial funding by the U.S. Department of Education, Rehabilitation Services Administration.

46B. Dr. Richard Robertson, formerly of the University of Pittsburgh Medical Center, as quoted in CTD NEws April 1995.
48. U.S. Pat. No. 5,352,050. 49. U.S. Pat. No. 2,040,248 granted May 12, 1936. 51. Typing for everyone, by Levine, Arco Publishing, Inc, New York, 1980.
52. Palmer D H et al, "Social and economic costs of carpal tunnel surgery," Instructional Course Lecture, 1995, Vol. 44, pp. 167-72". Cited in CTDNews, Haverford, Pa., November 1995, 4:11, p. 1.
53. Cumulative Trauma Disorders of the Upper Extremity, by Michael Erdil, M.D., O. Bruce Dickerson, M.D., M.P.H., and Elizabeth Glackin, M.D. Ch. 5 in Occupational Medicine, 3d Ed., by Carl Zenz, M.D., Sc.D., Ed. in Chief, with Dickerson, Editor, and Edward P. Horvath, Jr, M.D. M.P.H., Mosby, 1994, p. 48 et seq, at 49. 54. Kendall D: Etiology, diagnosis and paresthesia in the hands, Br Med J 2:1633-1640, 1960. Cited ibid (53) at 53.
55. Braun R M, Davidson K, Doehr M A: Provocative testing in the diagnosis of dynamic carpal tunnel syndrome, J Hand Surg Am 14A (2 Pt 1): 195-197, 1989. Cited ibid (53) at 54.
56. George Piligian, M.D., occupational medicine physician at the Mount Sinai Irving J. Selikoff Occupational Health Clinic in New York. Quoted in (42-32). 57. Michael Wills, a Toronto doctor who specializes in occupational medicine, quoted in (42-13).
58. Phone interview with US West, D. Franco, Supervisor, Omaha Neb. Mar. 26, 1996. Phone interview with Bell Core, B. Schultheis, New Jersey, Dec. 15, 1995.
59. Definitions and descriptions from Blakiston's New Gould Medical Dictionary, copr. 1890-1956. McGraw-Hill Book Company, Inc. New York, Toronto, London; Editors Normand Hoerr, M.D. Arthur Osol, Ph.D and 88 contributors.

What is claimed is:

1. A method for testing and preventing the onset of symptoms of nerve pathology, improving discovery of cancer mass and reducing inflammation, the method comprising the steps of: A) identifying the subject's nerve pathology by diagnostic tests; B) identifying the subject's base line physical condition by inspection or examination tests; C) conducting the base line physical condition tests; D) providing the subject a tool; E) selecting exercises as uses of the tool to maximize inflammation in the structures adjacent to the nerve; F) instructing the subject on a use of the tool to maximize inflammation in the structures adjacent to the nerve; G) instructing the subject on self reporting of pain, tingling, decrease or change of feeling; H) instructing the subject to perform the self reporting; I) the subject performs the self reporting; J) instructing the subject on exercises of the tool to maximize inflammation; K) instructing the subject to perform the exercise of the tool to maximize inflammation; L) the subject performs the exercise; M) repeat steps C, H and I; N) adjourning the testing while awaiting the return of the subject to the base line physical conditions in step B; O) selecting exercises as uses of the tool to minimize inflammation in the structures adjacent to the nerve; P) repeat steps C, H and 1; Q) instructing the subject on a use of the tool to minimize inflammation in the structures adjacent to the nerve; R) instructing the subject to perform the exercise of the tool to minimize inflammation; S) the subject performs the exercise; T) repeat steps C, H and I; U) identify number of tests to conduct to obtain statistically reliable and reproducible results; V) identify number of subjects to test to obtain statistically reliable and reproducible results; W) alternate between steps E to M and O to T to blind the results; X) conduct, preserve, protect and record all steps as necessary with sufficient tests, subjects, and alternates to obtain meaningful data; Y) establish end points for the data; and Z) calculate the statistical deviations necessary to compare the end points tools, wherein the data is used to establish an effectiveness of the tool at minimizing inflammation in the structures adjacent to the nerve.

2. The method of claim 1, wherein the diagnostic tests are chosen from any or all: Tinel's sign, Phalen's test, carpel compression test, Durkam's sign, flick test, tourniquet test, cotton ball finger stroke test, two-point discrimination test, palpation test, Semmen-Weinstein monofilanient test, cervical spine x-ray, nerve conduction study, doppler ultramonography, magnetic resonance imaging, corticosteroid injection, wrist squareness ratio, wrist splint at night test, nerve face electroneurometer, vibration test, grip and pinch strength, dynamometer, pinch gauge, visual analog scale pain assessment, hand volume water displacement test, thermography, finger wrinkling, long finger III abduction and adduction, thumb I abduction opposition, pinky finger V flexion, middle finger III flexion, profundus tendon test, sharp pin impale finger test, loss of drag, index finger abduction, pinky finger abduction, Electro mylo gram, middle finger flexion, nerve stimulation, electrodiagnosis, flexor carpi ulnaris palpation, palmaris longus palpation, extensor digitorum communis palpation, finger whistle, thumb bending, spread hand palpation, dorsal interossei spread fingers, fingernail pressure, hypertrophy tendon, blindfold test, comparison of abnormal and normal limb, Linburg's sign, wrist radiograph, Finkelstein's test, dorsiflex wrist, extensor carpi ulnaris palpation, oblique retinacular ligament tightness test, grind test, arterial patency finger press test, tape measure, caliper, infusion catheter, and distal sensory latency test.

3. The method of claim 1, wherein the exercises and use of the tool, includes any or all: 1) to increase inflammation requires maximum repetitive flexion use, that is extension and flexion of the fingers; 2) to increase inflammation includes typing on the QWERTY layout keyboard or typewriter, or on any keyboard wherein the majority of usage of letters is away from the home row, the ball or track mouse data entry peripheral and the one hand finger pad arrangement of numerals 0 through 9; 3) to prolong the increase of inflammation or decrease inflammation requires minimum repetitive flexion use; 4) to prolong the increase of inflammation or decrease inflammation includes typing on the AslnRedHot, Dvorak, keyboard or any efficient keyboard with the letter E on the home row, use of a drafting board, internal consumption of aspirin or any anti-inflammatory drug or medicine, section of the transverse carpal ligament, or any exercise; wherein the tools includes a wrist brace, a chair, a table, a typewriter, a light, a video display terminal, or any similar binding, sitting, supporting, communicating, illuminating, and displaying equipment.

4. The method of claim 1, wherein the nerve pathology is median nerve entrapment, ulnar nerve entrapment, or any neuropathy or neuritis.

5. The method of claim 1, wherein the nerve comprises the median nerve and the structures adjacent to the nerve include the nine flexor tendons next to the median nerve.

6. The method of claim 1, wherein work of any or all of the nine flexor muscles next to the median nerve is shifted to the lumbricals of the fingers, the dorsal interossei of the hand, and the volar interossei muscles.

7. The method of claim 1, wherein the base line physical condition by inspection or examination tests include, any or all: 1) water displacement, caliper or tape measure of hand volume; 2) self report upper extremity assessment battery, sensory evaluation palmar and dorsal views of hand; 3) self report visual analogue scale for pain; 4) self report verbal rating scale for pain; 5) daily activity and medication log and pain level scale report; and 6) turn key in lock.

8. The method of claim 1, wherein the base line physical condition by inspection or examination tests includes any or all, identifying the patient's name, address, phone, age, referring Health Care Professional, Health History, background data on carpal tunnel syndrome or cancer, gender, prior diagnosis, hands/fingers night tingle or pain, braces or special support on hands or arm, pain relievers, prior nerve conduction velocity study, heart trouble, chest pain, fainting or dizziness, hand or finger therapy, bone/joint problem, arthritis, physical reason to avoid exertion, number of fingers used in activities, prior surgery, prior hospitalization, high blood pressure, swelling or any vascular disease, asthma/bronchitis, abnormal blood lipid or sugar levels, medications, allergy drugs, pain relievers, nonsteroidal anti-inflammatory drugs, steroids, anti-inflammatories, Prednisone, pills, caffeine, alcohol, tobacco, multi-vitamins, dietary supplements, coronary disease, sudden death, heart disease, diabetes, cancer, pregnancy, menstruation, steroid injection, metabolic rate of discharge of drugs, with provisions to update the answers if they change, and instructions to avoid any pain relievers for times before each typing activity.

9. The method according to claim 1 wherein the method further comprises the step of the patient selecting for treatment of symptoms of any or all of the physical disabilities of: aberrant anatomy, acidosis, acromegalic arthritis, acromegaly, acrosclerosis, acute wasting paralysis, acute ascending paralysis, acute anterior poliomyelitis, adenohypophysis, aerobic exercise, aging, alcoholism, amyloidosis, anemia, aneurysms, angina, apoplexy, arachnodactyly, arteriolar disease, arteriosclerosis, arteriovenous malformation, artery, arthritis of rheumatic fever, arthritis, atrophic arthritis, atrophy, backward cardiac failure, baseball finger, Bence-Jones protein, benign tumor, birth, birth palsy, blood vessel, bone marrow, bony ankylosis, brachial plexus, brachial birth palsy, brachial paralysis, brachialgia, brain, brain abscess, Buerger's disease, bulbar apoplexy, burn, bursitis, calcinosis, calcium, calcium deposits, callus, canal volume increased, canal volume decreased, capillary walls, cardiac failure, carpal bones, carpal tunnel syndrome, carpometacarpal joint arthritis, cartilage, cataract, central nervous system, cerebral vessels, cerebral palsy, cervical adenitis, cervical spine arthritis, cervical radiculopathy, cervical radiculopathy, Charcot's arthritis, Charcot-Marie-Tooth disorder, chorionitis, chronic arthritis, cigarette smoking, clubbed finger, collagen, coma, congestive, connective tissue, consciousness, contraceptive pills, cretinism, cyst of joint capsule, cyst of semi-lunar cartilage, cystic tumor of tendon sheath, cystic, dactylitis syphilitica, debility, deep palmar retroflexor space abscess, deformity, degenerative joint disease, degenerative conditions, deltoid, demineralization, dermatosclerosis, diabetes, diabetes mellitus, diabetic polyneuropathy, digital neuropathies individual, digital arteries, digits, disuse osteoporosis, dolichostenomelia, dropsy, drumstick finger, dyspnea, dystrophia myotonica, ear, edema, embolism, endocrine organs, eosinophilic cells, epicondylitis, epidemic paralysis, epidermis, Erb-Duchenne syndrome, erythroid myeloma, extracranial lesions, extravasation, fascia, fibromyalgia syndrome, flaccid paralysis, fracture, ganglion, gastric, gastrointestinal, glycosuria, gonococcus, gonorrheal arthritis, gout, gouty tophus, gouty arthritis, granulation, gumma, hammer finger, Haversian spaces, head injury, heart failure, heart, Heberdens arthritis, Heine-Medin's disease, hematogenous arthritis, hematoma, hemic myeloma, hemodialysis, hemolytic streptococcus, hemophilic arthritis, hemorrhage, hereditary conditions, high blood pressure, Hippocratic finger, hunger, hydrostatic pressure, hypercalcemla, hyperemia, hyperesthesia, hyperfunction, hypergiobulinemia, hyperglycemia, hypermotility, hyperplasia, hypertension, hypertrophic pulmonary osteoarthropathy, hypertropyhic reaction, hypothyroidism, incoordination, infantile paralysis, infection, infectious arthritis, infectious conditions, inflanimation, inflammatory conditions, insulin, intracranial lesions, ischemic paralysis, joint capsule, joint surface, Kahler's disease, ketosis, Klumpke palsy, knuckle, lead palsy, leprosy, lesion, leukocytosis, lipoma, lock finger, luxation, lymph, lymphocytic myeloma, lymphoid myeloma, malignant, mallet finger, malnutrition osteoporosis, Marfan's syndrome, marrow, mass lesion, medulla oblongata, men, menopausal arthritis, menopause, menstruation, metabolic, migraines, mucoid hyaluronic acid, mucopolysaccharidosis, multiple sclerosis, muscle spasms, muscle tenderness, muscular dystrophy, myelocytic sarcoma, myeloid myeloma, myeloid tumor, myeloma, myeloma multiple, myofascial dysfunction, myoselerosis, myotonia dystrophica, myotonic dystrophy, myxedema, neoplastic conditions, neuritis, neurological, neurons, neuropathic arthritis, neuropathies individual, neurotrophic arthritis, obesity, obstetric paralysis, osmotic pressure, ossification, osteoarthritis, osteoporosis, palsy, paralysis, paralytic poliomyelitis, phalangectomy, phalangitis, phalangitis syphilitica, phalangization, phalangophalangeal amputation, phalanx, phosphatase, phosphorus, plasma, plasma cell myeloma, plasmacytes, plasmacytic myeloma, plasmacytic sarcoma, plasmacytoma, plasmocytic sarcoma, plasmocytic myeloma, plasmocytoma, plasmona, pneumococcus, polio, poliomyelitis, polyneuritis, pons, postinjury, postmenopausal osteoporosis, power grip, pregnancy, prenatal syphilis, printer's palsy, proliferative arthritis, pronator syndrome, protein concentration, proximal lumbrical insertion, proximal median neuropathy, psychosis of hysterical numbness and clenched-fist syndrome, pulmonary, punctiform, Quervain's disease, Quinquaud's phenomenon, radiation neuritis, radiohumeral articulation, radiohumeral bursitis, radiohumeral epicondylitis, Raynaud's syndrome, Recklinghausen's disease, reflex sympathetic dystrophy, renal failure, respiratory, reticular fibers, rheumatic fever, rheumatoid arthritis, rheumatoid tenosynovitis, ruptured disk, sanguineous apoplexy, scarlatinal synovitis, scarlatinal arthritis, scarlet fever, scleriasis, scleroderma, seal finger, seizures idiopathic peripheral causes, senile, osteoporosis, senility, skeleton, sodium urate, spastic diplegia, spider finger, spinal nerves, spinal cord, spinal cord lesions, splanchnomegaly, sprain fracture, springfinger, steinert's disease, steilate cells, stroke, subchondral spaces, subdural hematoma, sugar tolerance, swallow, swelling, symmetrical synovitis, syndactyly, synovectomy, synovial, synovial tissues, synovial distention, synovial proliferation nonspecific, synovitis, synovium nonspecific fibrosis, syphilitic arthritis, syringomyelia, systemic disease, tabes dorsalis, tactile anesthesia, tendinitis, tendon sheath, tendons, tendovaginitis stenosans, tenosynovitis, thirst, thoracic outlet syndrome, thrombosed, thrombosis, thyroid hormone, thyroid conditions, tongue, tophaceous gout, trabeculae, transient ischemic attacks, trauma, traumatic conditions, tremors, trigger finger, tuberculosis, tuberculous tenosynovitis, tuberous sclerosis, tumor, tumor benign, ulnar nerve neuropathy, uremia, uric acid, urine, vascular spasm, vascular conditions, vasculitis, vasomotor disturbances, viscera, Volkmann's paralysis, weakness, webbed fingers, weeping sinew, weight, whitefinger syndrome, women, or wrist malalignment.

* * * * *